United States Patent [19]

Clark, Jr. et al.

[11] Patent Number: 5,512,261
[45] Date of Patent: Apr. 30, 1996

[54] PROCESS FOR REMOVING SULFUR DIOXIDE FROM FLUIDS

[75] Inventors: Earl Clark, Jr.; Jimmie J. Straw, both of Bartlesville, Okla.

[73] Assignee: Phillips Petroleum Company, Bartlesville, Okla.

[21] Appl. No.: 373,828

[22] Filed: Jan. 17, 1995

[51] Int. Cl.$^6$ .............................. C01B 17/60; B01D 50/00
[52] U.S. Cl. ........................................ 423/242.1; 210/194
[58] Field of Search ................... 549/87, 84; 423/242.1; 210/194

[56] References Cited

U.S. PATENT DOCUMENTS

| | | | |
|---|---|---|---|
| 3,622,598 | 11/1971 | Willis | 549/87 |
| 4,861,900 | 8/1989 | Johnson | 549/87 |
| 4,900,524 | 2/1990 | Fulleman | 423/242 |
| 5,290,953 | 3/1994 | Clark, Jr. et al. | 549/87 |
| 5,320,816 | 6/1994 | Tsai et al. | 423/235 |
| 5,347,018 | 9/1994 | Clar, Jr. et al. | 549/84 |

*Primary Examiner*—Richard L. Raymond
*Assistant Examiner*—Deborah Lambkin
*Attorney, Agent, or Firm*—Lucas K. Shay

[57] ABSTRACT

A process for removing sulfur dioxide in a fluid such as, for example, sulfolene or sulfolane, comprises circulating the fluid in a loop under conditions sufficient to effect the removal of sulfur dioxide from the fluid wherein the loop comprises at least one spraying device such as, for example, a spray nozzle.

30 Claims, No Drawings

PROCESS FOR REMOVING SULFUR DIOXIDE FROM FLUIDS

FIELD OF THE INVENTION

This invention relates to a process for removing sulfur dioxide from a sulfur dioxide-containing fluid. This invention also relates to a process for producing sulfolane compounds from a conjugated diene and sulfur dioxide. More specifically, this invention relates to a process for producing sulfolane compounds having reduced sulfur dioxide content.

BACKGROUND OF THE INVENTION

Sulfur dioxide in a fluid often has an adverse effect if the fluid is used in some industrial applications. For example, sulfur dioxide in a fluid may induce metal corrosion when the fluid is used in applications requiting the contacting of the fluid with a metal or metal surface. These fluids can be a gas, an aqueous liquid, a non-aqueous liquid, or combinations of any two or more thereof, such as, for example, a sulfolene compound or a sulfolane compound.

Sulfolane compounds are useful in a variety of industrial applications such as, for example, in pesticidal compositions, intermediates in the production of other organic chemicals, selective solvents to separate aromatic compounds from petroleum fractions, and selective solvents in alkylation of olefins.

Sulfolane compounds are generally prepared by catalytic hydrogenation of the corresponding sulfolene compounds. The sulfolene compounds are prepared by the reaction of a conjugated diene such as, for example, 1,3-butadiene, and sulfur dioxide at elevated temperatures.

However, the sulfolene compounds thus-produced are generally unstable and tend to decompose at mildly elevated temperatures into an unsaturated organic compound and sulfur dioxide. Furthermore, when the sulfolene compounds are used to prepare the corresponding sulfolane compounds by catalytic hydrogenation, the initiation of hydrogenation reaction may also increase the temperature enough to result in some decomposition of the sulfolene. Some of these decomposed products polymerize and the resulting polymer coats the hydrogenation catalyst significantly reducing its activity. Moreover, unreacted sulfur dioxide and the sulfur dioxide obtained from decomposition of sulfolene compounds also interfere with the subsequent catalytic hydrogenation. If excess sulfur dioxide is present in the resulting sulfolane compounds, the sulfolane compounds become corrosive towards metals and results in some undesirable side effects when the sulfolane compounds are used in industrial applications. These sulfur dioxides must be removed or substantially reduced.

Processes have been developed for inhibiting the formation of polymers and reduction of sulfur dioxide in the production of sulfolane compounds. For example, amines have been used as inhibitors in reducing the amount of polysulfone polymer formation. Oxidizing agents have been used to reduce sulfur dioxide and other impurities. However, there is an ever-increasing need to develop still more effective methods of removing sulfur dioxide content in sulfolene and sulfolane compounds thereby greatly improving the production of superior sulfolane compounds.

SUMMARY OF THE INVENTION

An object of the present invention is to provide a process for removing or substantially removing sulfur dioxide in a fluid. Also an object of the present invention is to provide a process for preparing a fluid having a reduced sulfur dioxide concentration. Another object of the invention is to reduce the sulfur dioxide content of sulfolane compounds. Another object of the invention is to remove dissolved sulfur dioxide from sulfolene compounds. A further object of the invention is to produce sulfolane compounds having reduced sulfur dioxide content. Still a further object of the invention is to develop a process to improve the productivity of sulfolane compounds produced. An advantage of the invention is the reduction of sulfur dioxide without chemical treatment thereby eliminating the need of further removing the chemical. Other objects, features and advantages will become more apparent as the invention is more fully disclosed hereinbelow.

According to the present invention, a process for removing or substantially removing sulfur dioxide in a fluid is provided which comprises circulating the fluid from a container at an effective temperature for a sufficient time through a loop wherein the loop re-enters the container through at least one spraying device for producing increased surface area of the fluid to effect the removal of sulfur dioxide from the fluid.

DETAILED DESCRIPTION OF THE INVENTION

According to the present invention, the term "fluid" denotes a gas, a liquid, or combinations thereof. The term "fluid" also denotes water, solution, suspension, dispersion, emulsion, or non-aqueous fluid such as hydrocarbons, and combinations of any two or more thereof. The presently preferred fluid is a crude sulfolene compound or a crude sulfolane compound which, when produced, generally contains sulfur dioxide dissolved or dispersed in the crude sulfolene or crude sulfolane compound.

Generally, a fluid or portions thereof can be removed from a container or vessel by any means known to one skilled in the art such as, for example, a pump. The fluid or portions thereof is moved through a loop, and returned to the container or vessel through a spraying device such as, for example, a spraying nozzle thereby increasing the surface area of the fluid. Generally, it is preferred that a fluid or portions thereof be removed from the bottom of a container and returned to the top of the fluid surface through a loop and a spraying device.

Any spraying device can be used so long as the spraying device can increase the surface area of a fluid. The term "surface area" used in the present invention, unless otherwise indicated, is referred to as the one in a fluid container and the one being generated by the spraying device. Generally, in the present invention, such a surface area is increased by at least about 50%, preferably about 100%, and most preferably 1,000% as compared to the fluid surface area which is not circulated through the spraying device. Examples of suitable spraying devices include, but are not limited to, spraying nozzles, splash plates, atomizers, spraying jets, orifices, and combinations of any two or more thereof.

The number of spraying devices can be any number depending on the type of fluid, volume of fluid, concentration of sulfur dioxide in the fluid, and other parameters. Generally, at least one is required. It can be as many as one skilled in the art desires.

The temperature for circulating the fluid to remove sulfur dioxide from a fluid is the temperature that can effect a reduction of the sulfur dioxide content in the fluid and is generally dependent upon the types of fluid as well as upon the concentration of sulfur dioxide in the fluid. Generally, the temperature can be in a range of from about 25° C. to about 400° C., preferably about 35° C. to about 350° C., and most preferably 45° C. to about 300° C. The time required for carrying out the process of the invention is a sufficient time required to effect the reduction of sulfur dioxide concentration in a fluid and generally depends on the desired reduction and on the types of fluid. Generally, it can be in a range of from about 1 minute to about 20 hours, preferably about 5 minutes to about 10 hours, most preferably 10 minutes to 5 hours, especially when a crude sulfolene or crude sulfolane which is detailed hereinbelow is the fluid. The process of the invention can be carried out under any pressure, i.e., reduced or elevated pressure, so long as the pressure can effect a reduction in sulfur dioxide content in a fluid. The rate of circulation generally depends on the pump and is the rate that can effect the reduction of sulfur dioxide in a fluid. Generally, the rate can be in the range of about 0.01 to about 25, preferably about 0.05 to about 50, and most preferably 0.1 to 100 gallons per minute.

Any fluid, as defined hereinabove, can be used in the present invention so long as the fluid contains dissolved sulfur dioxide and it is desirable to remove this sulfur dioxide from the fluid. The presently preferred fluid is a crude sulfolene or crude sulfolane compound. Any crude sulfolene or crude sulfolane can be used in the present invention. Processes for producing a sulfolene or a sulfolane containing or contaminated with sulfur dioxide are well known to one skilled in the art. For example, processes disclosed in U.S. Pat. Nos. 3,622,598; 5,290,953; and 5,347,018 can be employed for producing a crude sulfolene or a crude sulfolane. Disclosures of these three U.S. Patents are herein incorporated by reference.

For example, a process for producing a crude sulfolene and a crude sulfolane can comprise the steps of: (1) contacting a conjugated diene with sulfur dioxide under conditions sufficient to synthesize a crude sulfolene compound whereby a mixture of the crude sulfolene compound and impurities comprising unreacted sulfur dioxide is produced; (2) transferring the mixture to an impurities removal reactor containing a solvent; (3) removing the impurities under a reduced pressure to produce an impurities-reduced sulfolene compound; (4) transferring the impurities-reduced sulfolene compound to a hydrogenation reactor; (5) contacting said impurities-reduced pure sulfolene compound with hydrogen, in the presence of a hydrogenation catalyst, under conditions sufficient to produce a crude sulfolane compound which also contains impurities; and (6) optionally recovering said sulfolane compound wherein the impurities which comprise sulfur dioxide are substantially reduced or removed.

The term "sulfolene compound" (sometimes referred to as "sulfolenes" or "sulfolene compounds") as employed herein is defined in U.S. Pat. No. 3,622,598, which is incorporated herein by reference. This term includes substituted and unsubstituted 3-sulfolenes and 2-sulfolenes. The preferred sulfolene compound used in this invention is unsubstituted 3-sulfolene, which is commercially available and is produced by the reaction of 1,3-butadiene and sulfur dioxide. The terms "sulfolane" and "sulfolane compounds" are also defined in U.S. Pat. No. 3,622,598.

The sulfolene compounds can be prepared by reacting sulfur dioxide with a conjugated diene having the structural formula R—C(R)=C(R)—C(R)=C(R)—R wherein each R can be the same or different and is selected from the group consisting of hydrogen and various organic and/or inorganic radicals which do not interfere with the reaction for producing the sulfolene compound or the subsequent hydrogenation reaction to produce the corresponding sulfolane compound. Inorganic radicals which are suitable include the halogens, hydroxyl groups, and combinations of any two or more thereof. Organic radicals which are preferred include hydrocarbyl substituents having 1 to about 8 carbon atoms per radical.

A presently preferred class of starting materials comprises the conjugated dienes of the structural formula indicated above where each R is individually selected from the group consisting of hydrogen, alkyl, alkenyl, aryl, cycloalkyl, cycloalkenyl, aralkyl, alkaryl, alkylcycloalkyl, and combinations of any two or more thereof. The total carbon content of the conjugated diene is in the range of 4 to about 18.

Representative examples of the conjugated dienes include, but are not limited to, 1,3-butadiene, 2-methyl-1,3-butadiene (isoprene), 2,3-dimethyl-1,3-butadiene, 2,3-diethyl-1,3-butadiene, 3,4-dimethyl-2,4-hexadiene, 2,4-dodecadiene, 2-methyl-1,3-hexadiene, 4-ethyl-1,3-hexadiene, 1-cyclopentyl-1,3-pentadiene, 1-(1-cyclohexene-1-yl)-1,3-butadiene, 2-phenyl-1,3-butadiene, 3-benzyl-1,3-pentadiene, 3-p-tolyl-1,3-pentadiene, and combinations of any two or more thereof. Suitable substituted derivatives of the above illustrated dienes can also be reacted with sulfur dioxide to form desired sulfolene compounds. Examples of such substituted dienes include 2-chloro-1,3-butadiene, 2-methyl-3-chloro-1,3-butadiene, 1-cyano-1,3-butadiene, and combinations of any two or more thereof.

Examples of representative sulfolene compounds include, but are not limited to, 2-methyl-3-sulfolene, 2-sulfolene, 3-sulfolene, 3-methyl-2-sulfolene, 3-methyl-3-sulfolene, 2-methyl-3-sulfolene, 2,4-dimethyl-2-sulfolene, 2,4-dimethyl-3-sulfolene, 3-ethyl-3-sulfolene, and combinations of any two or more thereof.

The term "reactor" used herein is referred to as, unless otherwise indicated, reaction vessel or vessels that can be properly employed in chemical or physical reactions. The choice of a suitable reactor is generally a matter of preference to one ordinarily skilled in the art.

The first step of the process, according to the present invention, is the contacting of a conjugated diene with sulfur dioxide either in the presence or in the absence of a solvent. It can be either a continuous or a batch operation. The molar ratio of sulfur dioxide to the conjugated diene is the ratio that can effect the synthesis of a sulfolene and can be in the range of from about 1:1 to about 2:1, preferably about 1:1 to about 1.5:1, and most preferably 1:1 to 1.2:1. The temperature of the reaction is generally in the range of from about 50° C. to about 150° C., preferably about 60° C. to about 120° C., and most preferably from 65° C. to 80° C. The pressure of the reaction vessel is generally in the range of about 10 psig to about 500 psig, preferably about 20 psig to about 300 psig, and most preferably 30 psig to 120 psig.

The solvent suitable for use in the present invention is selected from the group consisting of water, an alcohol, a sulfone, an organic amide, and combinations of any two or more thereof. Suitable alcohols include, but are not limited to, methanol, ethanol, propanol, isopropanol, butanol, pentanol, and combinations of any two or more thereof. Suitable sulfone solvents include, but are not limited to, sulfolane, 2-methyl sulfolane, 3-methyl sulfolane, 3-ethyl sulfolane, and combinations of two or more thereof. Suitable organic amide solvents include, but are not limited to, N-methyl-2- pyrrolidone, N,N'-dimethylformamide, and combinations of any two or more thereof. The weight ratio of the solvent, if present, to the conjugated diene is generally in the range of about 0.05:1 to about 1,000:1, preferably 0.5:1 to 10:1.

The order of addition of reactants to the reaction vessel is not important. Generally, the conjugated diene is added to the reaction vessel which already contains the sulfur dioxide to form a reaction mixture. The reaction mixture is allowed to react for a sufficient time, generally about 2 hours to about 24 hours, to allow substantial completion of the reaction to produce a reaction mixture comprising the sulfolene compound.

Upon the desired completion of the reaction, a molten reaction effluent is transferred to an impurities removal vessel (sometimes referred to as a sulfur dioxide removal vessel) which contains a solvent. The scope of the solvent is the same as described above in the first step of the process. The amount of solvent required is a sufficient amount to provide a fluid solution and the weight ratio of the solvent to the sulfolene is generally in the range of about 1:1 to about 1:20. Water is the presently preferred solvent because it promptly decreases the freezing point of the molten sulfolene compound produced in the first step so that decomposition of the sulfolene compound is minimized. The temperature of the molten reaction mixture and the solvent in the removal reactor is maintained at about 35° C. to about 85° C., preferably about 35° C. to about 70° C., and most preferably 40° C. to 65° C. to minimize the decomposition of sulfolene and the formation of undesirable polymers.

After completion of the transfer, impurities including unreacted sulfur dioxide and the sulfur dioxide produced as a result of decomposition of the sulfolene compounds where the sulfur dioxide may be dissolved in the solvent employed are removed by sparging an inert gas to the contents in the removal vessel, under a vacuum in the range of about 1 mmHg to about 500 mmHg, preferably about 10 mmHg to about 300 mmHg, and most preferably 20 mmHg to 100 mmHg. The inert gas is generally sparged at a rate in the range of about 1 to about 100 standard cubic feet per hours (scfh), preferably about 1 to about 50 scfh, and most preferably 1 to 10 scfh. The time required for substantially removing the sulfur dioxide varies, depending on the concentration of the sulfur dioxide, the temperature, nitrogen sparged, and the pressure applied, and is generally about 10 minutes to about 10 hours. The temperature for removal of the sulfur dioxide is generally in the range of temperature disclosed hereinabove for the removal reactor. Though it is not necessary to stir the reaction mixture during the sulfur dioxide removal, a mechanical mixing, such as stirring, of the reaction mixture can be used to facilitate the removal of sulfur dioxide. A further enhancement of the sulfur dioxide removal can be accomplished by the process of the present invention as disclosed above.

Upon removing substantially all sulfur dioxide, a sulfolene compound having substantially reduced sulfur dioxide and other volatile impurities is produced. The sulfolene compound is thereafter transferred to a hydrogenation reactor followed by addition of a suitable hydrogenation catalyst. Suitable catalysts include any of those known in the art to be useful in the catalytic hydrogenation of sulfolenes to sulfolanes. A preferred class of hydrogenation catalysts are those which comprise the metal hydrogenation catalysts, such as those containing or consisting of nickel, cobalt, copper, platinum, palladium or mixtures of these metals with themselves or with other metals such as iron, zinc, chromium, cadmium, and mixtures thereof. These metals may be used in finely divided form such as, for example, Raney nickel, or may be suitably supported on a support such as kieselguhr, aluminum oxide, and diatomaceous earth. These catalysts can be prepared in any suitable manner known to one skilled in the art. The amount of catalyst utilized will vary with the catalyst but will generally be in the range of about 0.1 to about 20 weight percent based on the weight of sulfolene compounds to be hydrogenated.

According to the present invention, the total hydrogenation catalyst required is added in about 2–10 increments to the hydrogenation reactor containing the sulfolene compounds. The total hydrogenation catalyst required is the amount of catalyst necessary to substantially hydrogenate all sulfolene compounds in the hydrogenation reactor. This is done by monitoring the hydrogen uptake. Hydrogen can be constantly introduced into the hydrogenation reactor and monitored by heat release or by pressurizing the reactor up and watching the pressure decrease. Additional catalyst is added when the hydrogen uptake stops or slows down significantly.

The hydrogenation of the sulfolene compounds is carried out by the conditions well known to one skilled in the art. An example is disclosed in U.S. Pat. No. 3,622,598, which is incorporated herein by reference.

Following completion of the hydrogenation reaction, the sulfolane compounds can be recovered by conventional procedures. Generally, the reaction gases are vented from mixtures and then the reaction mixture is filtered to remove the spent hydrogenation catalyst followed by fractionation of the filtered reaction mixture to remove solvent and unreacted sulfolene compounds. The fractionation (purification) is performed in three steps. First, the crude sulfolane is dehydrated at about 100° C. and atmospheric pressure. Secondly, the sulfolane is cooked at a temperature in the range of from bout 100° C. to about 300° C., preferably about 140° C. to about 250° C., and most preferably 170° C. to 200° C. under a reduced pressure of about 50 to about 200 mmHg for about 1 to about 15 hours, preferably about 1 to about 12 hours, and most preferably 1 to 10 hours, to effect the decomposition of residual sulfolene and removal of butadiene and sulfur dioxide. Afterwards, the sulfolane is further purified by distillation at a reduced pressure in the range of from about 1 mmHg to about 200 mmHg, and preferably 10 mmHg to 50 mmHg and 130° C. to about 250° C., and most preferably 160° C. to 180° C. for a period as disclosed immediately hereinabove.

The following examples are presented to further illustrate the invention and are not to be construed to unduly limit the scope of the invention. All reactors or vessels employed in the examples were 2 gallons in volume and equipped with an electrical heating jacket, cooling coils, a mechanical stirrer, baffles, inlets and outlets, and appropriate temperature controls.

In the examples shown below, sulfur dioxide stability of sulfolane was determined as follows. The apparatus for measuring sulfur dioxide stability comprised a 3-neck 500 ml round bottom flask fitted with a nitrogen source, a gas dispersion tube, a heating mantle, a temperature controller, a thermocouple, a magnetic stirrer, and a 250 ml gas washing bottle.

Two hundred milliliters of 3% hydrogen peroxide was placed in the gas washing bottle. Molten sulfolane (250 ml), weight % which is noted in Table I, was added to the round bottom flask which had been tared. The contents in the round bottom flask was heated to 180°. Immediately thereafter, nitrogen flow at 0.2 standard cubic feet per hour (scfh) was introduced into the round bottom flask and then to the gas wash tube which was immersed in the gas washing bottle. The $N_2$ flow was allowed for 1 hour at the indicated temperature. The apparatus and contents therein were then allowed to safely cool to about 25° C. to about 75° C. Thereafter, several drops of methyl purple indicator solution purchased commercially from Fisher Scientific was added to the contents of the gas washing bottle and the contents were titrated with 0.1N sodium hydroxide to a gray end point. Sulfur dioxide concentration in sulfolane was calculated using the equation:

mg $SO_2$/250 ml sulfolane=1012.306×ml NaOH/sample weight (g).

EXAMPLE I

This is an example showing a process for preparing sulfolane compounds.

The runs were carried out as follows. A 2 gallon stainless steel reactor which contained a heel of 4750 grams of sulfolene at 74° C. was charged with 4.2 g of dimethylamine. Sulfur dioxide (1412 g or 22.06 moles) and 1,3-butadiene (1135 g or 20.02 moles) were pumped in at a rate of about 4 to 6 grams per minute while maintaining operating temperature with an external electric heater. The pressure during the above feedstock addition increased to about 160 psig (1102 kPa) by the end of the butadiene addition (e.g., 3.0 hours). The reaction mixture was kept at 74° C. with stirring for 7 to 24 hours while the pressure slowly decreased to about 80 psig (55 1 kPa).

A portion of the reaction mixture was then transferred, using a dip tube, to an impurities removal vessel containing 1000 g of water at 50° C., leaving a heel of 4750 g of sulfolene.

A 100 mm Hg vacuum was applied to the impurities removal reactor for 2 to 6 hours, with continuous mixing to remove most of the sulfur dioxide, while the reactor temperature was maintained at 50° C. The final sulfur dioxide concentration was 100 to 500 ppm determined by iodimetric titration with starch as indicator. Iodimetric titration was carried out by first weighing a sample (1.5 g) into an Erlenmeyer flask containing 75 ml deionized water. An aliquot (0.25 ml) of starch indicator solution (prepared by heating 4 g soluble starch, 40 g sodium chloride and 200 ml deionized water at boiling with stirring for 2–3 minutes followed by cooling to 25° C.) was added to the flask. The solution in the flask was then titrated with 0.01N iodine to the starch/iodine end point. Concentration of sulfur dioxide was calculated as: ppm $SO_2$=ml iodine× normality iodine× 32.035×1,000.

The $SO_2$-reduced sulfolene/water mixture was transferred to a hydrogenation reactor prior to adding catalyst. Raney nickel catalyst (150 g) was weighed out on a scale, kept wet to prevent it from rapidly oxidizing and charged to the hydrogenation reactor. The reactor was pressured to 400 psig with hydrogen. Hydrogen uptake was monitored by pressure decrease. When the pressure had decreased to 200 psig, the reactor was charged back with hydrogen to 400 psig. When the pressure ceased to fall, the hydrogenation of sulfolene was considered complete. Since the hydrogenation heat of reaction is 32.1 Kcal per gram mole, the reactor medium was maintained at 50° C. by internal cooling coils with cool water. Total sulfolane produced was about 2000 g.

EXAMPLE II

This example illustrates the process of the invention.

The runs were carried out the same as that described in Example I except that a 0.25 inch O.D. stainless steel tubing roll line and a model 104/56C micro centrifugal pump were attached so that the contents of the sulfolene impurities removal vessel could be circulated from the bottom back into the top through a spraying nozzle at about 0.5–0.6 gallon per minute. As shown in Table I, the spraying nozzle effectively improved the removal of sulfur dioxide at an accelerated rate, as indicated by Runs 2 and 4 where the use of a spraying nozzle resulted in a lower sulfur dioxide content in less time as compared to Runs 1 and 3, respectively.

TABLE I

| Sulfur Dioxide Removal in Sulfolene Impurities Removal Vessel | | | | |
|---|---|---|---|---|
| Run[a] | 1 | 2 | 3 | 4 |
| Sulfolene, g | 2100 | 2000 | 2100 | 2000 |
| Sulfolane, g | | | 900 | 900 |
| Water, g | 900 | 900 | | |
| Vacuum, mmHg | 100 | 100 | 100 | 100 |
| Nitrogen, scfh | 3 | 3 | 3 | 3 |
| Pump Rate, gal/min. | 0 | 0.6 | 0 | 0.5 |
| $SO_2$, ppm | | | | |
| 0.0 Hr | 532 | 5292 | 3746 | 5475 |
| 0.5 Hr | | 196 | | 601 |
| 1.0 Hr | | 73 | | 219 |
| 1.5 Hr | | | | 164 |
| 2.0 Hr | 113 | | 361 | |
| $SO_2$ Stability[b] | 17.7 | 1.76 | 9.6 | 1.59 |

[a]Run 1 employed water as solvent, no spray during circulation; Run 2 employed water as solvent and used a spray nozzle during circulation; Run 3 employed sulfolane as solvent without using a spray nozzle; Run 4 employed sulfolane and spray nozzle during circulation.
[b]$SO_2$ stability denotes mg of $SO_2$ per 250 ml of sulfolane.

EXAMPLE III

This example illustrates the process of the invention using a roll line, pump and spray nozzle on the sulfolane impurities removal vessel.

The runs were carried out as those described in Example I with the exception a roll line and pump were attached so that the contents of the sulfolane impurities removal vessel could be circulated from the bottom back into the top through a spray nozzle at about 0.5 gallon per minute. It can be seen in Runs 22 and 23 in Table H that residual sulfolene was decomposed and sulfur dioxide was expelled to a lower value in a shorter period by use of a spray nozzle when compared to Run 21 which was carried out without a spraying nozzle. This can also be seen in the lower $SO_2$ stability values.

More runs were carried out using the sulfolane impurities removal vessel and either nitrogen sparging (Table III) or refluxing during the purification process (Table IV). However, the results in Tables III and IV show that neither nitrogen sparging nor refluxing enhanced the removal of residual sulfolene (decomposed to sulfur dioxide and butadiene) from sulfolane.

Thus, whereas, nitrogen sparge nor lower vacuum and/or allowing the system to reflux enhanced the removal of residual sulfolene (decomposed to sulfur dioxide and butadiene), the removal of residual sulfolene was greatly facilitated by the use of a roll loop and spray nozzle.

TABLE II

Effect of Spray Nozzle in Sulfolene Impurifies Removal Vessel on Sulfur Dioxide Removal

| Run[a] | Time, min | Vac., mmHg | Temp., °C. | Sulfolene, % | $SO_2$ Stability |
|---|---|---|---|---|---|
| 21 | Initial | | | 17.14 | |
| | 0 | 100 | 45 | | |
| | 27 | 100 | 70 | | |
| | 39 | 100 | 90 | | |
| | 60 | 230 | 124 | 16.37 | |
| | 75 | 300 | 136 | | |
| | 90 | 175 | 150 | | |
| | 93 | 100 | 156 | | |
| | 113 | 175 | 183 | | |
| | 115 | 100 | 190 | 2.11 | |
| | 145 | 100 | 191 | 0 | |
| | 175 | 100 | 190 | | 124.3 |
| | | | | | 26.1 |
| 22 | Initial | | | 18.01 | |
| | 0 | 22 | 100 | | |
| | 30 | 63 | 100 | | |
| | 41 | 77 | 125 | | |
| | 55 | 107 | 140 | | |
| | 60 | 117 | 180 | | |
| | 62 | 120 | 210 | | |
| | 66 | 127 | 275 | | |
| | 68 | 128 | 320 | | |
| | 70 | 132 | 375 | | |
| | 78 | 142 | 350 | | |
| | 85 | 153 | 190 | | |
| | 90 | 165 | 100 | 5.5 | |
| | 110 | 190 | 100 | 2.72 | |
| | 140 | 190 | 100 | 0 | |
| | 170 | 190 | 100 | | |
| | 190 | 180 | 100 | | |
| | 215 | 185 | 100 | | 0 |
| 23 | Initial | | | 17.58 | |
| | 0 | 15 | 100 | | |
| | 33 | 47 | 100 | | |
| | 58 | 60 | 100 | | |
| | 63 | 66 | 115 | | |
| | 70 | 77 | 135 | | |
| | 78 | 90 | 145 | | |
| | 90 | 112 | 145 | | |
| | 94 | 116 | 165 | | |
| | 96 | 120 | 200 | | |
| | 100 | 127 | 270 | | |
| | 103 | 132 | 360 | | |
| | 105 | 135 | 390 | | |
| | 107 | 137 | 380 | 6.42 | |
| | 111 | 137 | 310 | | |
| | 118 | 141 | 250 | | |
| | 124 | 153 | 100 | 0 | |
| | 156 | 190 | 100 | | 28.7 |
| | 186 | 190 | 100 | | |
| | 216 | 190 | 100 | 0 | |

[a] Run 21 was carried out without using a spray nozzle whereas Runs 22 and 23 employed a spray nozzle

TABLE III

Effect of Nitrogen Sparge on Removing Residual Sulfur Dioxide from Sulfolane

| Run[a] | Solvent | $N_2$ (scfh) | mg $SO_2$ per 250 ml |
|---|---|---|---|
| 31 | Water | 0 | 9.92 |
| 32 | Water | 1.5 | 8.88 |
| 33 | Sulfolane | 0 | 2.24 |
| 34 | Sulfolane | 1.5 | 17.76 |

[a] The runs were carried out at 190° C. for two hours.

TABLE IV

Effect of Reflux on Removing Sulfur Dioxide from Sulfolane

| Run[a] | Temp., °C. | Vacuum, mmHg | Reflux | Solvent | mg $SO_2$ per 250 ml |
|---|---|---|---|---|---|
| 41 | 190 | 100 | None | Sulfolane | 2.2 |
| 42 | 183 | 60 | Total | Sulfolane | 12.81 |
| 43 | 190 | 100 | None | Water | 9.9 |
| 44 | 187 | 55 | Total | Water | 15.3 |

[a] The runs were carried out for 2 hours.

The results shown in the above examples clearly demonstrate that the present invention is well adapted to carry out the objects and attain the ends and advantages mentioned as well as those inherent therein. While modifications may be made by those skilled in the art, such modifications are encompassed within the spirit of the present invention as defined by the disclosure and the claims.

That which is claimed is:

1. A process for reducing sulfur dioxide concentration comprising circulating a sulfur dioxide-containing fluid in a loop under conditions sufficient to reduce the concentration of sulfur dioxide in said fluid wherein said loop comprises at least one spraying device.

2. A process according to claim 1 wherein said fluid is selected from sulfolene compounds, sulfolane compounds, and combinations of any two or more thereof.

3. A process according to claim 1 wherein said fluid is sulfolene.

4. A process according to claim 1 wherein said fluid is sulfolane.

5. A process according to claim 1 wherein said spraying device produces a fluid of increased surface area from said fluid.

6. A process according to claim 5 wherein said fluid surface area increases by at least about 50% as compared to the surface area which is not circulated through said spraying device.

7. A process according to claim 5 wherein said fluid surface area increases by at least about 100% as compared to the surface area which is not circulated through said spraying device.

8. A process according to claim 5 wherein said fluid surface area increases by at least about 1,000% as compared to the surface area which is not circulated through said spraying device.

9. A process according to claim 2 wherein said spraying device produces a fluid of increased surface area from said fluid.

10. A process according to claim 9 wherein said fluid surface area increases by at least about 50% as compared to the surface area which is not circulated through said spraying device.

11. A process according to claim 9 wherein said fluid surface area increases by at least about 100% as compared to the surface area which is not circulated through said spraying device.

12. A process according to claim 9 wherein said fluid surface area increases by at least about 1,000% as compared to the surface area which is not circulated through said spraying device.

13. A process for reducing sulfur dioxide concentration in a sulfur-dioxide-containing sulfolene compound comprising circulating said sulfolene compound in a loop under conditions sufficient to reduce the concentration of sulfur dioxide in said sulfolene compound wherein said loop comprises at least one spraying device.

14. A process according to claim 13 wherein said sulfolene compound is sulfolene.

15. A process according to claim 13 wherein said spraying device produces a fluid of increased surface area from said sulfolene compound.

16. A process according to claim 15 wherein said sulfolene compound surface area increases by at least about 50% as compared to the surface area which is not circulated through said spraying device.

17. A process according to claim 15 wherein said sulfolene compound surface area increases by at least about 1,000% as compared to the surface area which is not circulated through said spraying device.

18. A process according to claim 14 wherein said spraying device produces a fluid of increased surface area from said sulfolene compound.

19. A process according to claim 18 wherein said sulfolene compound surface area increases by at least about 50% as compared to the surface area which is not circulated through said spraying device.

20. A process according to claim 18 wherein said sulfolene compound surface area increases by at least about 1,000% as compared to the surface area which is not circulated through said spraying device.

21. A process for reducing sulfur dioxide concentration in a sulfur-dioxide-containing sulfolane compound comprising circulating said sulfolane compound in a loop under conditions sufficient to reduce the concentration of sulfur dioxide in said sulfolane compound wherein said loop comprises at least one spraying device.

22. A process according to claim 21 wherein said sulfolane compound is sulfolane.

23. A process according to claim 21 wherein said spraying device produces a fluid of an increased surface area from said sulfolane compound.

24. A process according to claim 23 wherein said sulfolane compound surface area increases by at least about 50% as compared to the surface area which is not circulated through said spraying device.

25. A process according to claim 23 wherein said sulfolane compound surface area increases by at least about 1,000% as compared to the surface area which is not circulated through said spraying device.

26. A process according to claim 22 wherein said spraying device produces a fluid of an increased surface area from said sulfolane.

27. A process according to claim 26 wherein said sulfolane compound surface area increases by at least about 50% as compared to the surface area which is not circulated through said spraying device.

28. A process according to claim 26 wherein said sulfolane compound surface area increases by at least about 1,000% as compared to the surface area which is not circulated through said spraying device.

29. A process according to claim 1 wherein said fluid is liquid.

30. A process according to claim 1 wherein said fluid or portions thereof is removed from the bottom of a container containing said fluid and returned to the top of the fluid surface through said loop and spraying device.

* * * * *